US006427476B1

(12) United States Patent
Eddins (10) Patent No.: US 6,427,476 B1
(45) Date of Patent: Aug. 6, 2002

(54) PORTABLE AIR CONDITIONER

(76) Inventor: Garey L. Eddins, 445 Sycamore St., Jemison, AL (US) 35085

( * ) Notice: Subject to any disclaimer, the term of this patent is extended or adjusted under 35 U.S.C. 154(b) by 0 days.

(21) Appl. No.: 09/756,502

(22) Filed: Jan. 8, 2001

Related U.S. Application Data (63) Continuation-in-part of application No. 09/383,680, filed on Aug. 26, 1999, now Pat. No. 6,170,282.

(51) Int. Cl.[7] ................................................. F25D 3/08
(52) U.S. Cl. ........................................ 62/457.2; 62/406
(58) Field of Search ............................... 62/406, 457.2, 62/457.1, 259.3, 420, 459, 530

(56) References Cited

U.S. PATENT DOCUMENTS

| | | | | |
|---|---|---|---|---|
| 1,171,387 A | * | 2/1916 | Dickson | |
| 1,952,414 A | * | 3/1934 | Brizzolara | |
| 2,080,998 A | | 5/1937 | Brizzolara | |
| 2,469,259 A | * | 5/1949 | Burgess | |
| 2,841,964 A | * | 7/1958 | Anderson | |
| 3,529,435 A | | 9/1970 | Becker | |
| 4,468,932 A | * | 9/1984 | Bullard | 62/421 |
| 4,612,774 A | * | 9/1986 | Budreau | 62/420 X |
| 4,841,742 A | | 6/1989 | Biby | |
| D306,062 S | | 2/1990 | Moritani | |
| 5,005,368 A | * | 4/1991 | MacCracken et al. | 62/431 X |
| 5,197,301 A | | 3/1993 | Holcomb | |
| 5,685,165 A | | 11/1997 | Bigelow, Jr. | |

* cited by examiner

Primary Examiner—Chen-Wen Jiang (57) ABSTRACT

A portable air conditioner for portable cooling of a user. The portable air conditioner includes an insulated housing having a wall with an interior surface defining an interior space. An intake port extends through the wall of the housing. A fan assembly is mounted in the interior space of the housing in fluid communication with the intake port. The fan assembly is designed for drawing air through the intake port into the interior space of the housing. A discharge assembly mounted on the housing permits air to exit the interior space. A plurality of conduits in fluid communication with the fan assembly and the discharge assembly guide air through the interior space allowing the air to be cooled by chilled material placed in the interior space of the housing. A switch is operationally coupled between a power supply and the fan assembly for selectively supplying power to the fan assembly.

9 Claims, 6 Drawing Sheets

PORTABLE AIR CONDITIONER

CROSS REFERENCE TO RELATED APPLICATIONS

This application is a continuation-in-part of application Ser. No. 09/383,680, filed Aug. 26, 1999 now U.S. Pat. No. 6,170,280).

BACKGROUND OF THE INVENTION

1. Field of the Invention

The present invention relates to air conditioners and more particularly pertains to a new portable air conditioner for portable cooling of a user.

2. Description of the Prior Art

The use of air conditioners is known in the prior art. More specifically, air conditioners heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,685,165; U.S. Pat. No. 4,841,742; U.S. Pat. No. 5,197,301; U.S. Pat. No. Des. 306,062; U.S. Pat. No. 2,080,998; and U.S. Pat. No. 3,529,435.

While these devices fulfill respective, particular objectives and requirements, the aforementioned patents do not disclose a new portable air conditioner. The inventive device includes an insulated housing having a wall with an interior surface. The interior surface of the wall defines an interior space of the housing. The interior space of the housing is designed for holding chilled material. A closure member is removably mounted to the housing for permitting access to the interior space of the housing. An intake port extends through the wall of the housing whereby the intake port is designed for permitting air to pass into the interior space of the housing. A fan assembly is mounted in the interior space of the housing in fluid communication with the intake port. The fan assembly is designed for drawing air through the intake port into the interior space of the housing. A discharge assembly mounted on the housing for permitting air to exit the interior space. A plurality of conduits in fluid communication with the fan assembly and the discharge assembly for guiding air through the interior space of the housing. The conduits are designed for being cooled by the chilled material placed in the interior space of the housing thereby cooling air moving through the plurality of conduits. A power supply is operationally coupled to the fan assembly for providing power to the fan assembly. A switch is operationally coupled between the power supply and the fan assembly such that the switch permits selective supply of power to the fan assembly.

In these respects, the portable air conditioner according to the present invention substantially departs from the conventional concepts and designs of the prior art, and in so doing provides an apparatus primarily developed for the purpose of portable cooling of a user.

SUMMARY OF THE INVENTION

In view of the foregoing disadvantages inherent in the known types of air conditioners now present in the prior art, the present invention provides a new portable air conditioner construction wherein the same can be utilized for portable cooling of a user.

The general purpose of the present invention, which will be described subsequently in greater detail, is to provide a new portable air conditioner apparatus and method which has many of the advantages of the air conditioners mentioned heretofore and many novel features that result in a new portable air conditioner which is not anticipated, rendered obvious, suggested, or even implied by any of the prior art air conditioners, either alone or in any combination thereof.

To attain this, the present invention generally comprises an insulated housing having a wall with an interior surface. The interior surface of the wall defines an interior space of the housing. The interior space of the housing is designed for holding chilled material. A closure member is removably mounted to the housing for permitting access to the interior space of the housing. An intake port extends through the wall of the housing whereby the intake port is designed for permitting air to pass into the interior space of the housing. A fan assembly is mounted in the interior space of the housing in fluid communication with the intake port. The fan assembly is designed for drawing air through the intake port into the interior space of the housing. A discharge assembly mounted on the housing for permitting air to exit the interior space. A plurality of conduits in fluid communication with the fan assembly and the discharge assembly for guiding air through the interior space of the housing. The conduits are designed for being cooled by the chilled material placed in the interior space of the housing thereby cooling air moving through the plurality of conduits. A power supply is operationally coupled to the fan assembly for providing power to the fan assembly. A switch is operationally coupled between the power supply and the fan assembly such that the switch permits selective supply of power to the fan assembly.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new portable air conditioner apparatus and method which has many of the advantages of the air conditioners mentioned heretofore and many novel features that result in a new portable air conditioner which is not anticipated, rendered obvious, suggested, or even implied by any of the prior art air conditioners, either alone or in any combination thereof.

It is another object of the present invention to provide a new portable air conditioner which may be easily and efficiently manufactured and marketed.

It is a further object of the present invention to provide a new portable air conditioner which is of a durable and reliable construction.

An even further object of the present invention is to provide a new portable air conditioner which is susceptible of a low cost of manufacture with regard to both materials and labor, and which accordingly is then susceptible of low prices of sale to the consuming public, thereby making such portable air conditioner economically available to the buying public.

Still yet another object of the present invention is to provide a new portable air conditioner which provides in the apparatuses and methods of the prior art some of the advantages thereof, while simultaneously overcoming some of the disadvantages normally associated therewith.

Still another object of the present invention is to provide a new portable air conditioner for portable cooling of a user.

Yet another object of the present invention is to provide a new portable air conditioner which includes an insulated housing having a wall with an interior surface. The interior surface of the wall defines an interior space of the housing. The interior space of the housing is designed for holding chilled material. A closure member is removably mounted to the housing for permitting access to the interior space of the housing. An intake port extends through the wall of the housing whereby the intake port is designed for permitting air to pass into the interior space of the housing. A fan assembly is mounted in the interior space of the housing in fluid communication with the intake port. The fan assembly is designed for drawing air through the intake port into the interior space of the housing. A discharge assembly mounted on the housing for permitting air to exit the interior space. A plurality of conduits in fluid communication with the fan assembly and the discharge assembly for guiding air through the interior space of the housing. The conduits are designed for being cooled by the chilled material placed in the interior space of the housing thereby cooling air moving through the plurality of conduits. A power supply is operationally coupled to the fan assembly for providing power to the fan assembly. A switch is operationally coupled between the power supply and the fan assembly such that the switch permits selective supply of power to the fan assembly.

Still yet another object of the present invention is to provide a new portable air conditioner that is light weight and can be carried on the users back to allow the cooled air to blow upon the user's neck.

Even still another object of the present invention is to provide a new portable air conditioner that can be set on desk to provide cool area to a room.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

With reference now to the drawings, and in particular to FIGS. 1 through 6 thereof, a new portable air conditioner embodying the principles and concepts of the present invention and generally designated by the reference numeral 10 will be described.

As best illustrated in FIGS. 1 through 6, the portable air conditioner 10 generally comprises an insulated housing 11 having a wall 41 with an interior surface 12. The interior surface 12 of the wall 41 defines an interior space 13 of the housing 11. The interior space 13 of the housing 11 is designed for holding chilled material. A closure member 14 is removably mounted to the housing 11 for permitting access to the interior space 13 of the housing 11.

An intake port 15 extends the wall 41 of the housing 11 whereby the intake port 15 is designed for permitting air to pass into the interior space 13 of the housing 11. A fan assembly 16 is mounted in the interior space 13 of the housing 11 in fluid communication with the intake port 15. The fan assembly 16 is designed for drawing air through said intake port 15 into the interior space 13 of the housing 11. A discharge assembly 17 mounted on the housing 11 for permitting air to exit the interior space 13 of the housing 11.

A plurality of conduits 18 are in fluid communication with the fan assembly 16 and the discharge assembly 17 for guiding through the interior space 13 of the housing 11. The conduits 18 are designed for being cooled by the chilled material placed in the interior space 13 of the housing 11 thereby cooling air moving through the plurality of conduits 18.

A power supply 19 is operationally coupled to the fan assembly 16 for providing power to the fan assembly 16. A switch 40 is operationally coupled between the power supply 19 and the fan assembly 16 whereby the switch 40 permits selective supply of power to the fan assembly 16.

A drainage assembly 20 mounted on the housing 11 for draining liquid from the interior space 13 of the housing 11. The drainage assembly 20 comprises a drain tube 21 and a flexible container 22. The drain tube 21 is extended through the wall 41 of the housing 11 and being in communication with the interior space 13 of the housing 11. The flexible container 22 is coupled to the drain tube 21 opposite the interior space 13 of the housing 11 whereby the flexible container 22 receives fluid from the drain tube 21.

An isolation wall 23 is coupled to the interior surface 12 of the housing 11 and defining a separation space 24 within and fluidly separate from the interior space 13 of the housing 11. The fan assembly 16 and the power supply 19 are positioned in the separation space 24 for preventing any fluid in the interior space 13 from contacting the fan assembly 16 and the power supply 19.

The housing 11 has a base portion 25 and an extension portion 26. The base portion 25 is designed for resting against a back of the user. The extension portion 26 is upwardly extending from the base portion 25. The discharge assembly 17 is coupled to the extension portion 26 opposite the base portion 25 such that the discharge assembly 17 is positionable proximate a neck of the user whereby air flowing through the conduits 18 is discharged adjacent the neck of the user. The discharge assembly 17 comprises a diffusing chamber 27 in fluid communication with the conduits 18. The discharge assembly 17 has a plurality of apertures 28 in communication with the diffusing chamber 27 for discharging air adjacent to the neck of the user. The diffusing chamber 27 is arcuate in shape whereby the diffusing chamber 27 is designed for fitting over sides and back of the neck of user whereby the apertures 28 are directed directly onto the neck of the user.

A pair of straps 29 each attached to the housing 11 in a manner that the straps 29 are designed for securing the housing 11 to a user. A conduit bracket 30 is coupled to the interior surface 12 of the housing 11 and supporting the conduits 18 in the interior space 13 of the housing 11.

The wall 41 of the housing 11 comprises an inner wall 31 and additionally comprising an outer wall 32 exterior of the inner wall 31. An insulating material 33 is positioned between the inner wall 31 and the outer wall 32 for reducing heat transfer between the inner wall 31 and the outer wall 32 of the housing 11.

Figure 1:
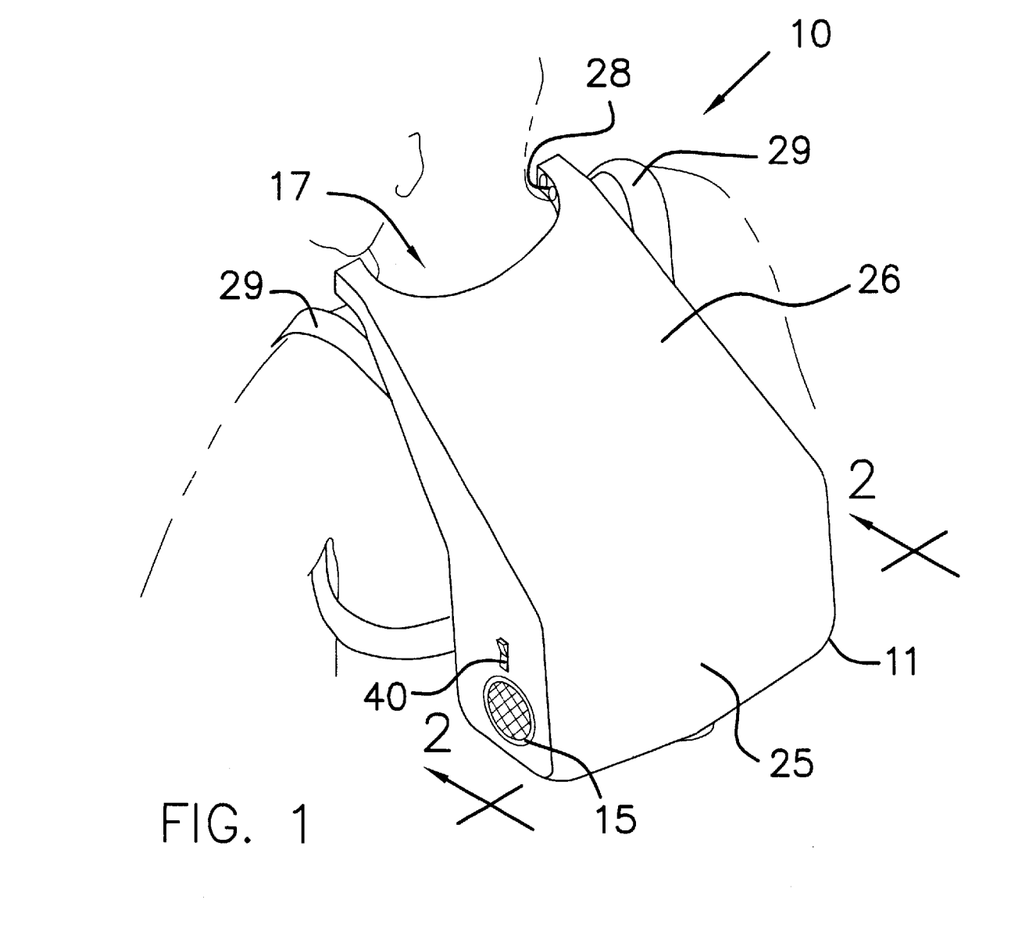
FIG. 1 is a schematic perspective view of a new portable air conditioner according to the present invention.
Figure 2:
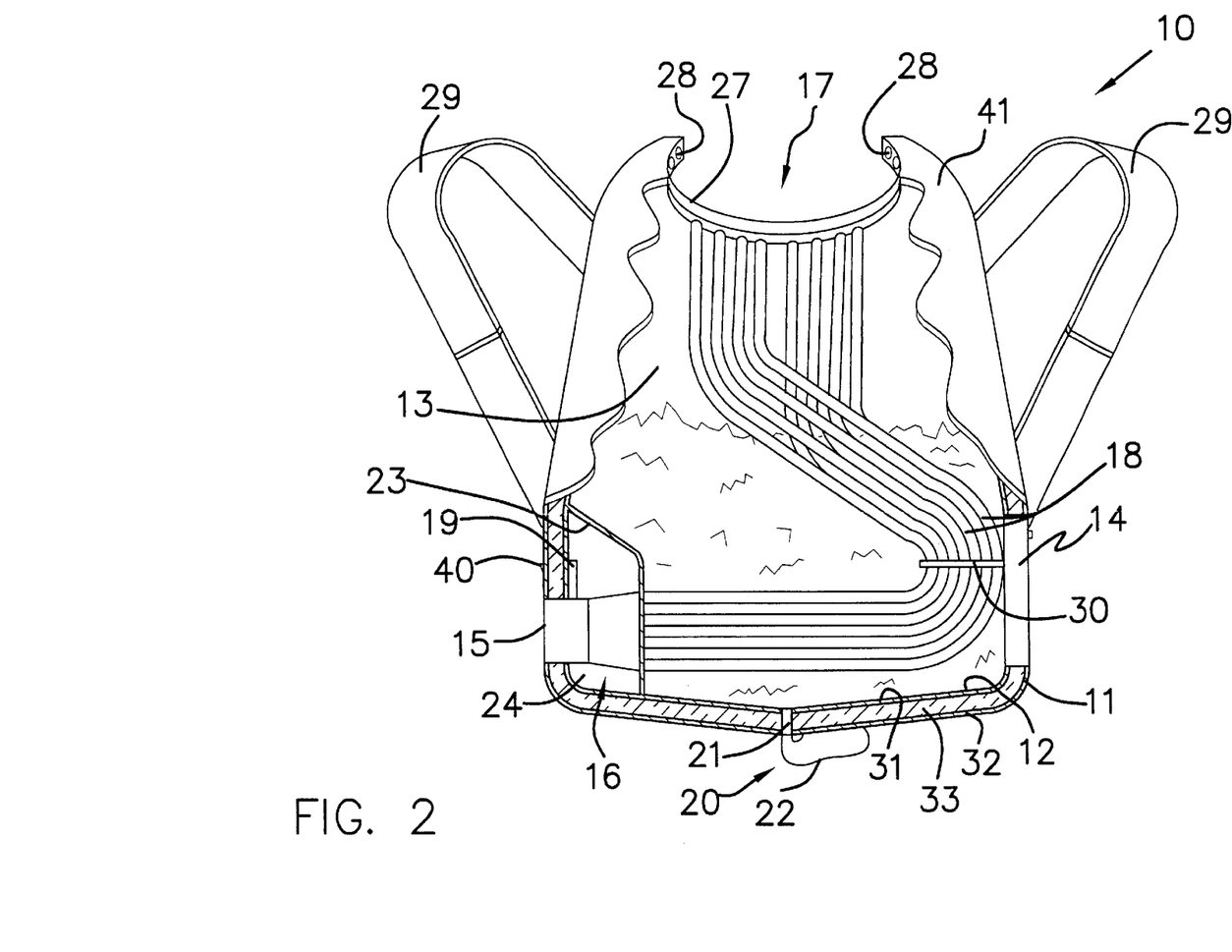
FIG. 2 is a schematic cross-sectional view of the present invention taken along line 2—2 of FIG. 1.
Figure 3:
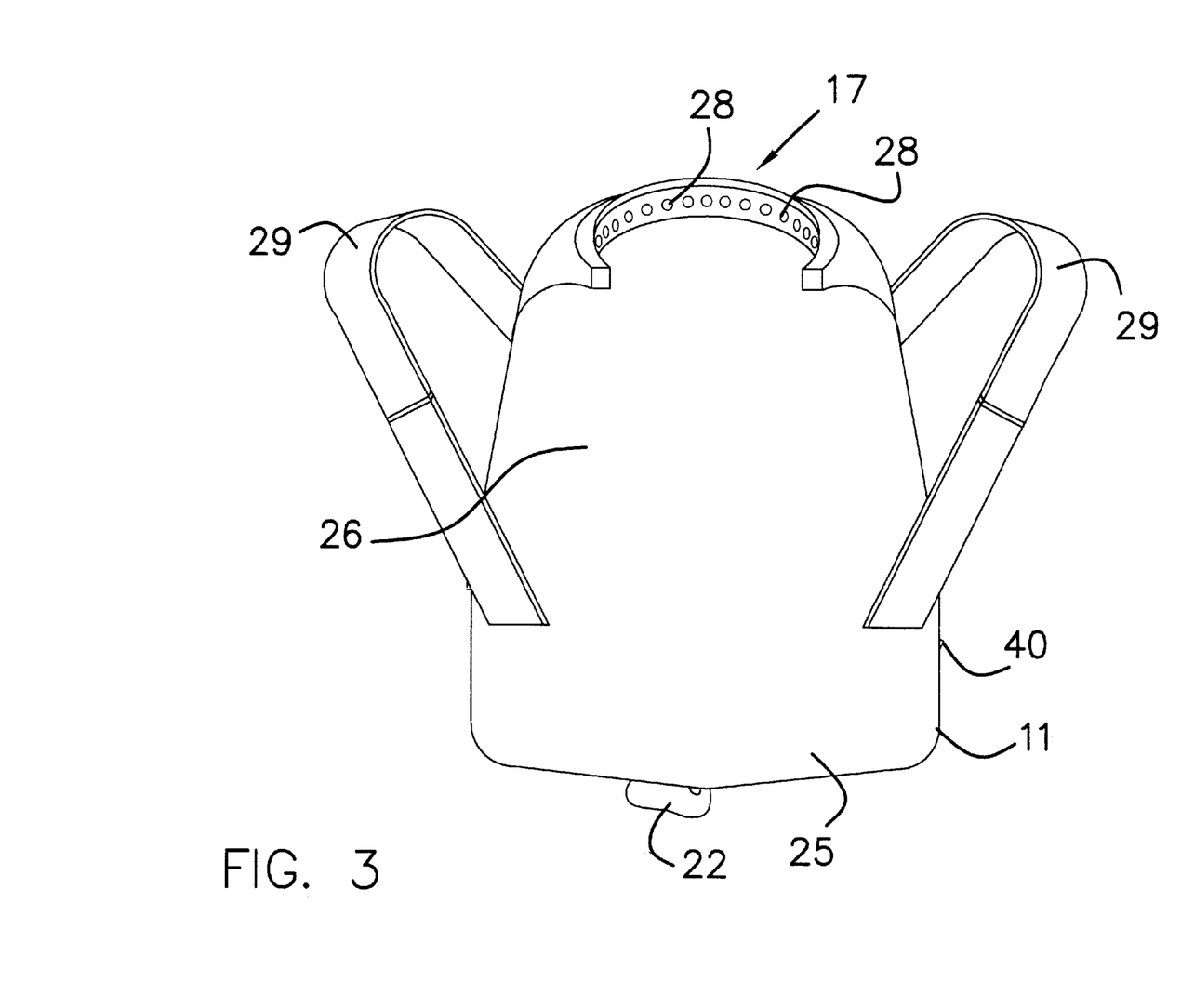
FIG. 3 is a schematic front view of the present invention.
Figure 4:
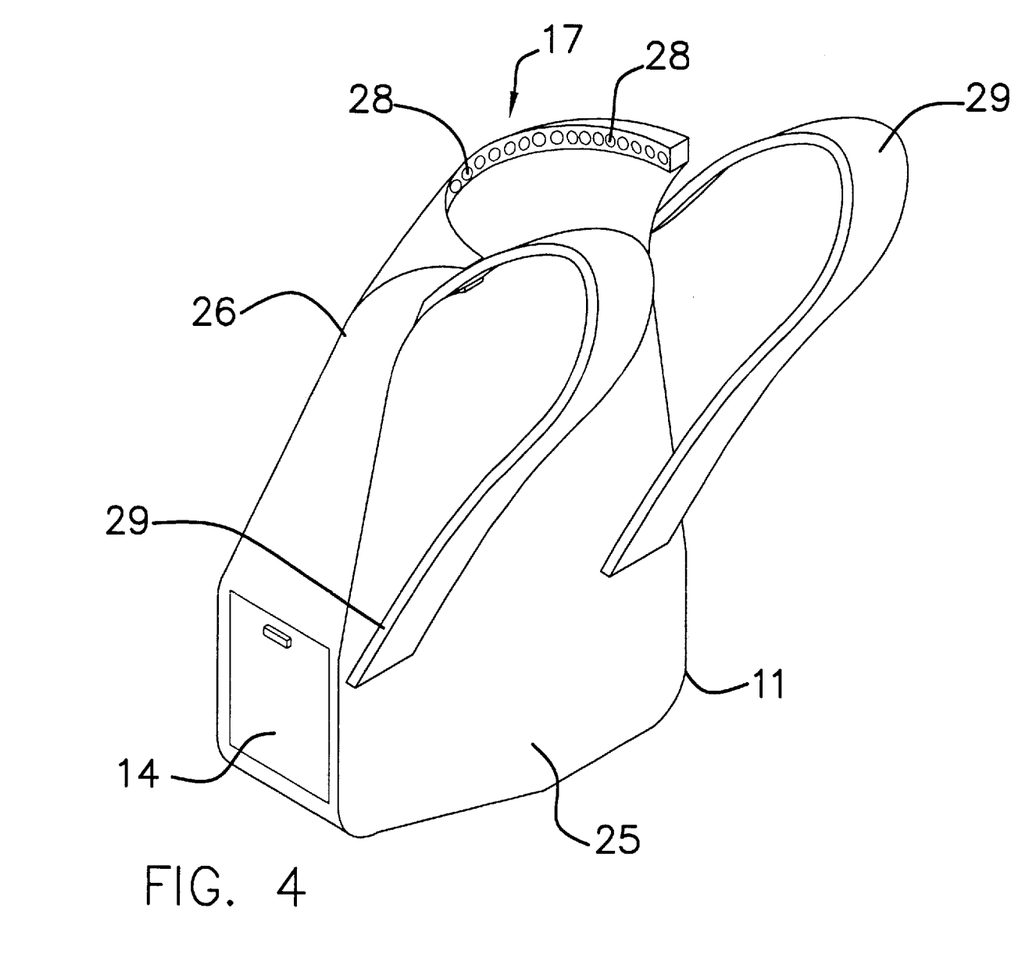
FIG. 4 is a schematic perspective view of the present invention.
Figure 5:
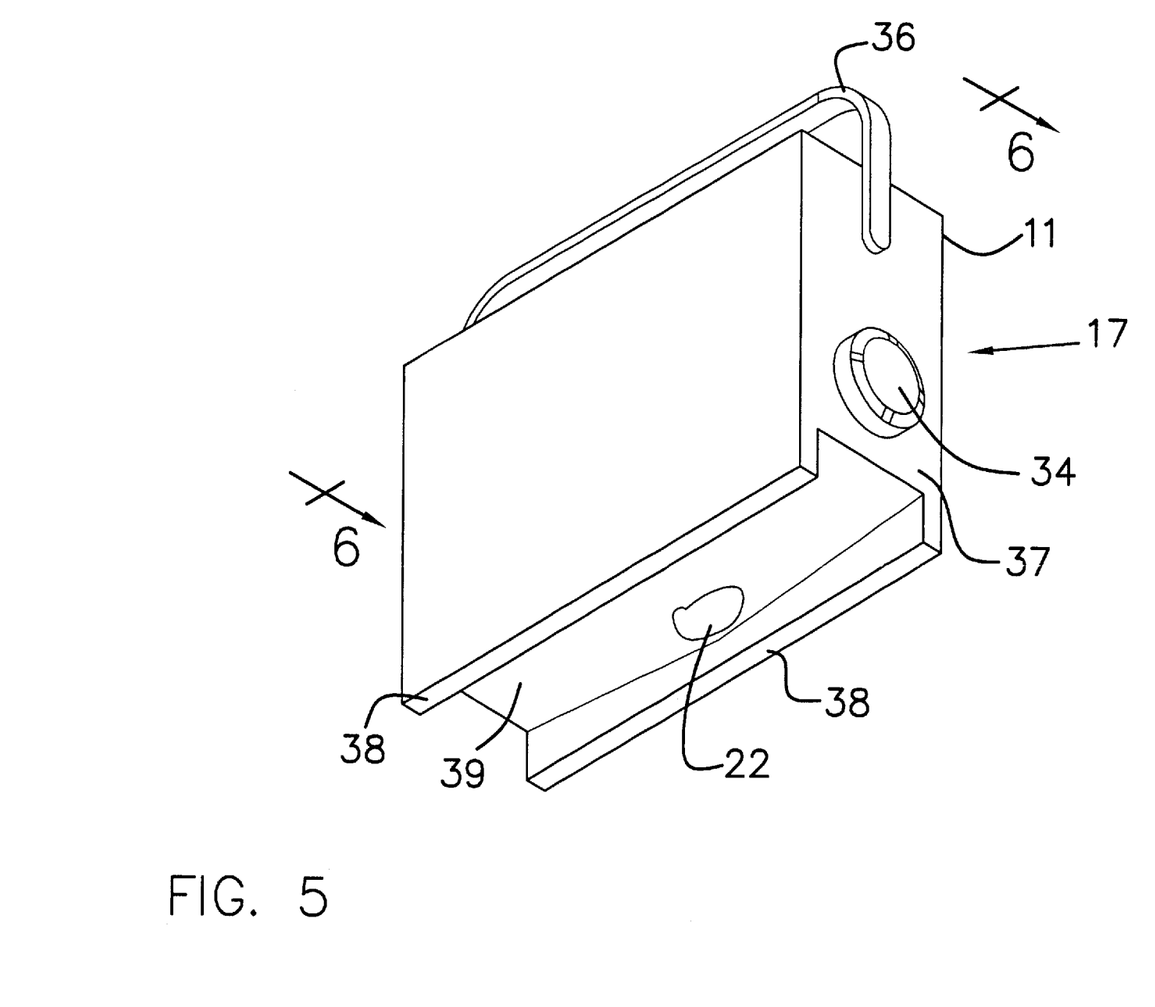
FIG. 5 is a schematic perspective view of the embodiment of the present invention.
Figure 6:
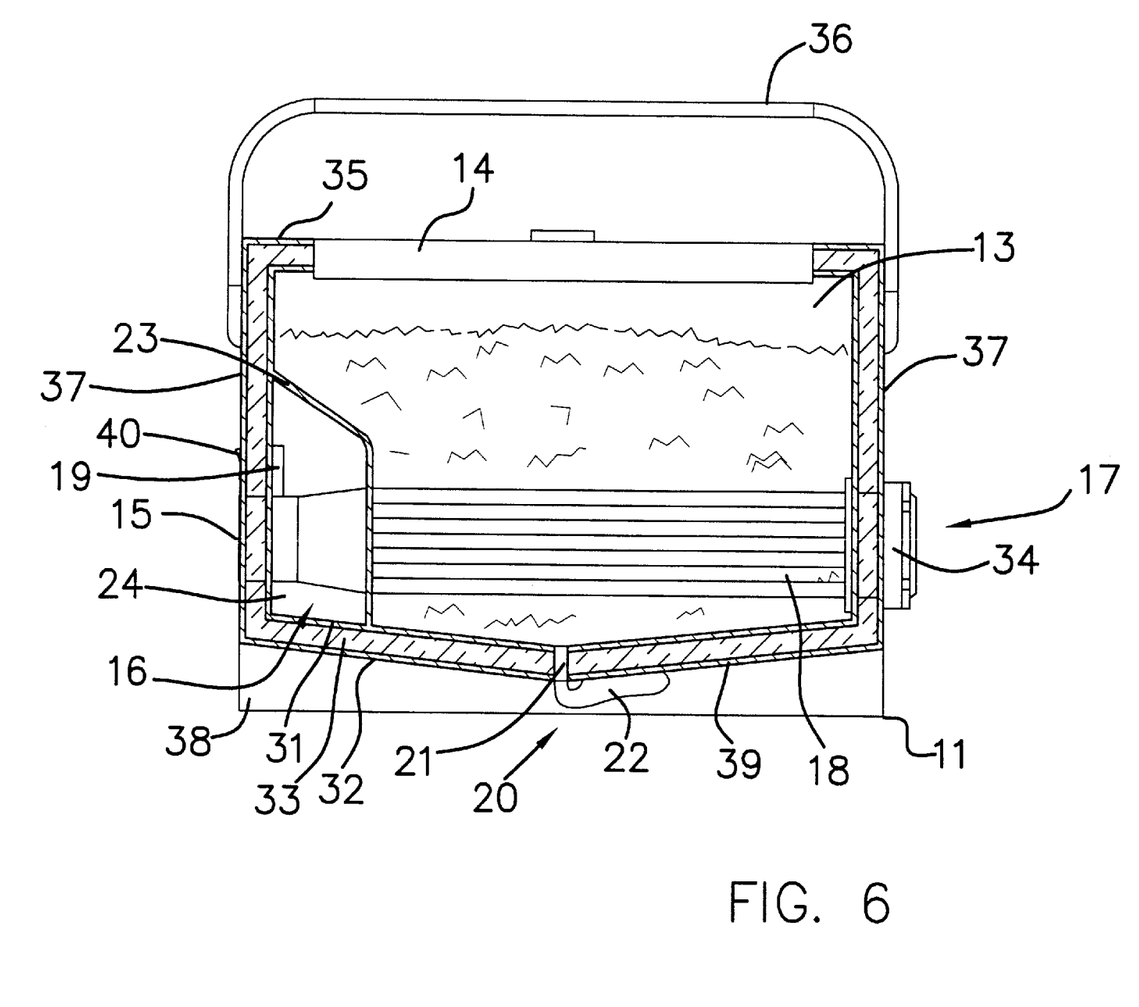
FIG. 6 is a schematic cross-sectional view of the embodiment of the present invention taken along line 6—6 of FIG. 5.

In an embodiment, said housing 11 is substantially rectangular shaped and is designed to be placed on a flat surface. The discharge assembly 17, of the embodiment, comprises an adjustable vent 34 designed for controlling the flow of the air exiting the housing 11 from the conduits 18. The closure member 14 is mounted on a top wall 35 of the housing 11 and a handle 36 extends between a pair of side walls 37 of said housing 11 to facilitate moving of the housing 11. The housing 11 has a pair of risers 38 downwardly extending from a bottom wall 39 of the housing 11 whereby the flexible container 22 has room to expand when the housing 11 is resting on a flat surface.

In use, the user places the housing on their back and secures the straps over the shoulders. The user then actuates the switch to turn on the fan assembly. The fan draws in air through the intake port and pushes the air through the conduits where the air is cooled by the ice in the interior space. The air then exits into the diffusing chamber which spread the air out over the area of the neck and the air exit the diffusing chamber through the apertures onto the user's neck thereby cooling the person.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be restored to, falling within the scope of the invention.

I claim:

1. A portable air conditioner comprising:
   an insulated housing having a wall with an interior surface, said interior surface of said wall defining an interior space of said housing, said interior space of said housing being adapted for holding a chilled material;
   a closure member being removably mounted to said housing, said closure member being for permitting access to said interior space of said housing;
   an intake port extending through said wall of said housing such that said intake port is adapted for permitting air to pass into said interior space of said housing;
   a fan assembly being mounted in said interior space of said housing in fluid communication with said intake port such that said fan assembly is adapted for drawing air through said intake port into said interior space of said housing;
   a discharge assembly mounted on said housing for permitting air to exit said interior space of said housing;
   a plurality of conduits being in fluid communication with said fan assembly and said discharge assembly for guiding air through said interior space of said housing, said conduits being adapted for being cooled by the chilled material placed in said interior space of said housing thereby cooling air moving through said plurality of conduits;
   a power supply being operationally coupled to said fan assembly for providing power to said fan assembly;
   a switch being operationally coupled between said power supply and said fan assembly such that said switch permits selective supply of power to said fan assembly; and
   said housing having a base portion and an extension portion, said base portion being adapted for resting against a back of the user, said extension portion being upwardly extending from said base portion, said discharge assembly being coupled to said extension portion opposite said base portion such that said discharge assembly is positionable proximate a neck of the user such that air flowing through said conduits is discharge adjacent the neck of the user.

2. The portable air conditioner as set forth in claim 1, further comprising:
   a drainage assembly mounted on said housing for draining liquid from said interior space of said housing.

3. The portable air conditioner as set forth in claim 2, wherein said drainage assembly comprises a drain tube and a flexible container, said drain tube being extended through said wall of said housing and being in communication with said interior space of said housing, said flexible container being coupled to said drain tube opposite said interior space of said housing such that said flexible container receives fluid from said drain tube.

4. The portable air conditioner as set forth in claim 1, further comprising:
   an isolation wall being coupled to said interior surface of said housing and defining a separation space within and fluidly separate from said interior space of said housing, said fan assembly and said power supply being positioned in said separation space for preventing any fluid in said interior space from contacting said fan assembly and said power supply.

5. The portable air conditioner as set forth in claim 1, wherein said discharge assembly comprises a diffusing chamber in fluid communication with said conduits, said discharge assembly having a plurality of apertures in communication with said diffusing chamber for discharging air adjacent to the neck of the user.

6. The portable air conditioner as set forth in claim 1, further comprises:
   a pair of straps, each strap being attached to said housing in a manner such that said straps are adapted for securing said housing to a user.

7. The portable air conditioners as set forth in claim 1, further comprises:
   a conduit bracket coupled to said interior surface of said housing and supporting said conduits in said interior space of said housing.

8. The portable air conditioner as set forth in claim 1, wherein said wall of said housing comprises an inner wall and additionally comprising an outer wall exterior of said inner wall, an insulating material being positioned between said inner wall and said outer wall for reducing heat transfer between said inner and outer walls of said housing.

9. A portable air conditioner comprising:
   an insulated housing having a wall with an interior surface, said interior surface of said wall defining an interior space of said housing, said interior space of said housing being adapted for holding a chilled material;
   a closure member being removably mounted to said housing, said closure member being for permitting access to said interior space of said housing;
   an intake port extending through said wall of said housing such that said intake port is adapted for permitting air to pass into said interior space of said housing;
   a fan assembly being mounted in said interior space of said housing in fluid communication with said intake port such that said fan assembly is adapted for drawing air through said intake port into said interior space of said housing;
   a discharge assembly mounted on said housing for permitting air to exit said interior space of said housing;
   a plurality of conduits being in fluid communication with said fan assembly and said discharge assembly for guiding air through said interior space of said housing, said conduits being adapted for being cooled by the chilled material placed in said interior space of said housing thereby cooling air moving through said plurality of conduits;
   a power supply being operationally coupled to said fan assembly for providing power to said fan assembly;
   a switch being operationally coupled between said power supply and said fan assembly such that said switch permits selective supply of power to said fan assembly;
   a drainage assembly mounted on said housing for draining liquid from said interior space of said housing;
   wherein said drainage assembly comprises a drain tube and a flexible container, said drain tube being extended through said wall of said housing and being in communication with said interior space of said housing, said flexible container being coupled to said drain tube opposite said interior space of said housing such that said flexible container receives fluid from said drain tube;
   an isolation wall being coupled to said interior surface of said housing and defining a separation space within and fluidly separate from said interior space of said housing, said fan assembly and said power supply being positioned in said separation space for preventing any fluid in said interior space from contacting said fan assembly and said power supply;
   wherein said housing has a base portion and an extension portion, said base portion being adapted for resting against a back of the user, said extension portion being upwardly extending from said base portion, said discharge assembly being coupled to said extension portion opposite said base portion such that said discharge assembly is positionable proximate a neck of the user such that air flowing through said conduits is discharge adjacent the neck of the user;
   wherein said discharge assembly comprises a diffusing chamber in fluid communication with said conduits, said discharge assembly having a plurality of apertures in communication with said diffusing chamber for discharging air adjacent to the neck of the user;
   said diffusing chamber being arcuate in shape such that said diffusing chamber is adapted for fitting over sides and back of the neck of user whereby said apertures are directed directly onto the neck of the user;
   a pair of straps, each strap being attached to said housing in a manner such that said straps are adapted for securing said housing to a user;
   a conduit bracket being coupled to said interior surface of said housing and supporting said conduits in said interior space of said housing; and
   wherein said wall of said housing comprises an inner wall and additionally comprising an outer wall exterior of said inner wall, an insulating material being positioned between said inner wall and said outer wall for reducing heat transfer between said inner and outer walls of said housing.

* * * * *